(12) United States Patent
Maloney et al.

(10) Patent No.: US 11,793,671 B2
(45) Date of Patent: Oct. 24, 2023

(54) EYEOPENER

(71) Applicant: Aero Healthcare (US), LLC, Valley Cottage, NY (US)

(72) Inventors: Thomas E. Maloney, Kingston (CA); Edmond P. Maloney, Vancouver (CA)

(73) Assignee: Aero Healthcare (US), LLC, Valley Cottage, NY (US)

( * ) Notice: Subject to any disclaimer, the term of this patent is extended or adjusted under 35 U.S.C. 154(b) by 1056 days.

(21) Appl. No.: 16/307,461

(22) PCT Filed: Jun. 6, 2017

(86) PCT No.: PCT/US2017/036229
§ 371 (c)(1),
(2) Date: Dec. 5, 2018

(87) PCT Pub. No.: WO2017/214205
PCT Pub. Date: Dec. 14, 2017

(65) Prior Publication Data
US 2019/0192342 A1 Jun. 27, 2019

Related U.S. Application Data

(60) Provisional application No. 62/346,437, filed on Jun. 6, 2016.

(51) Int. Cl.
*A61F 9/00* (2006.01)
*B65D 37/00* (2006.01)
(Continued)

(52) U.S. Cl.
CPC .......... *A61F 9/0026* (2013.01); *A61F 9/0008* (2013.01); *A61H 35/02* (2013.01);
(Continued)

(58) Field of Classification Search
CPC ...... A61F 9/0026; A61F 9/0008; A61F 9/013; A61H 35/02; A61H 2033/048;
(Continued)

(56) References Cited

U.S. PATENT DOCUMENTS 3,409,009 A * 11/1968 Vasse .................... A61F 9/0008
222/548
3,812,741 A * 5/1974 Heine ....................... B67B 7/18
81/3.4
(Continued)

FOREIGN PATENT DOCUMENTS

EP 0500172 A1 8/1992
EP 1179332 A2 * 2/2002 ............. A61H 35/02
(Continued)

OTHER PUBLICATIONS

International Search Report and Written Opinion dated Sep. 13, 2017, for International Application No. PCT/US2017/036229.
(Continued)

*Primary Examiner* — Nicholas J. Weiss
*Assistant Examiner* — Brandon W. Levy
(74) *Attorney, Agent, or Firm* — Erise IP, P.A.

(57) ABSTRACT

A device for washing eyes that allows for single-handed dispensing of fluid into a user's eye. The device consists of a container and a container locator. The container locator includes a cap with a base-supporting member that supports an arced base suspended above the cap. In use, the user holds the device with one hand and rests the arced base on the user's brow to control the direction of the fluid expelled from the container into the user's eye while fingers on the other hand reach through gaps in the base-supporting member to hold the user's eye open.

18 Claims, 6 Drawing Sheets

(51) Int. Cl.
*A61H 35/02* (2006.01)
*A61H 33/04* (2006.01)

(52) U.S. Cl.
CPC ........ *B65D 37/00* (2013.01); *A61H 2033/048* (2013.01); *A61H 2201/0153* (2013.01); *A61H 2201/1253* (2013.01)

(58) Field of Classification Search
CPC .... A61H 2201/0153; A61H 2201/1253; A61H 35/00; A61H 2201/1676; B65D 37/00; B65D 83/0094; B65D 47/18; B65D 2251/0096; A61M 2210/0612; A61M 35/003; A61M 1/008; A61M 11/008; A61M 3/0262; A61J 1/00; A61B 3/00; A61B 3/14

See application file for complete search history.

(56) References Cited

U.S. PATENT DOCUMENTS

| | | | | |
|---|---|---|---|---|
| 4,111,200 | A * | 9/1978 | Sbarra | A61F 9/0026 604/301 |
| 4,733,802 | A * | 3/1988 | Sheldon | A61F 9/0026 604/302 |
| 6,364,875 | B1 | 4/2002 | Stanley, III | |
| 6,371,945 | B1 * | 4/2002 | Sherman | A61F 9/0026 604/300 |
| 8,672,904 | B1 * | 3/2014 | Schultz | A61M 3/0262 604/302 |
| 2002/0004653 | A1 | 1/2002 | Carlsson et al. | |
| 2003/0024947 | A1 * | 2/2003 | Joshi | B65D 51/225 222/83 |
| 2004/0251276 | A1 * | 12/2004 | Adams | B65D 51/2835 222/153.14 |
| 2008/0281280 | A1 | 11/2008 | Jaworski et al. | |
| 2009/0218309 | A1 * | 9/2009 | Wang Wu | B65D 47/244 215/388 |
| 2010/0022971 | A1 * | 1/2010 | Marx | A61F 9/0026 604/302 |
| 2012/0310184 | A1 | 12/2012 | Pedersen | |
| 2015/0359667 | A1 | 12/2015 | Brue | |

FOREIGN PATENT DOCUMENTS

| | | | | |
|---|---|---|---|---|
| FR | 2687568 A1 | | 8/1993 | |
| GB | 2509618 A | * | 7/2014 | .......... A61F 9/0026 |
| GB | 2509618 B | | 11/2014 | |
| WO | 2011088833 A2 | | 7/2011 | |

OTHER PUBLICATIONS

European Extended Search Report dated Jan. 8, 2020, for Application No. 17810897.3.

* cited by examiner

EYEOPENER

CROSS-REFERENCE TO RELATED APPLICATION

This application is a national phase application under 35 U.S.C. § 371 of International Application No. PCT/US2017/036229, filed Jun. 6, 2017, which claims the benefit under 35 U.S.C. § 119(e) of U.S. Provisional Patent Application No. 62/346,437 filed Jun. 6, 2016, which applications are incorporated herein by reference in their entireties for all purposes.

FIELD OF THE INVENTION

The present invention relates generally to devices for opening an eye.

BACKGROUND

Serious eye injuries are very common in both home and the workplace. The U.S. Bureau of Labor Statistics has estimated that more than 20,000 eye injuries happen in the workplace each year. Injuries on the job can result in serious damage to the eye, and often require one or more missed work days for recovery. In fact, the Occupational Safety and Health Administration (OSHA) has reported that eye injuries in the workplace have cost an estimated $300 million per year in lost productivity, medical treatment and worker compensation.

A wide variety of workplace hazards exist that can cause injury to the eyes, including for example: i) hammering, grinding, sanding, and other masonry work that can produce particles; ii) handling chemicals that can lead to splashes in the eye; iii) wet or powdered cement in the eye which can cause a chemical burn; iv) dusty or windy conditions that can lead to particles in the eye; and v) eye injuries that result from simply passing through an area where work is being performed.

In order to ameliorate or treat damage to the eye due as soon as possible, emergency eye wash bottles and/or emergency eye wash stations have been developed. Indeed, they are commonly present (if not required) at most job sites.

One common type of eye wash bottle is a squeezable bottle having a nozzle suitable for delivery of fluid into the eye (see, e.g., Honeywell's 16 ounce, single refill, disposable eye wash station). Other types of eye wash bottles may use an eye cup attached to the bottle in order to create a reservoir to retain fluid for the purpose of washing the eye (see, e.g., U.S. Pat. No. 6,540,726 and Bel-Art Product F24851-0000 1000 ml empty eyewash bottle: https://www-.belart.com/bel-art-f24851-0000-one-1000 ml-empty-wash-bottle-for-emergency-eye-wash-safety-stations.html).

Other examples of eye wash stations are disclosed in U.S. Pat. Nos. 6,458,108, and 7,241,279. One difficulty however with these eye wash stations (and in particular, the cup-based eye wash bottles), is that: i) they may retain particle or chemical based residue in the eye cup; and ii) they do not adequately allow an individual that may be in intense pain to retract their eyelids in order to properly rinse the eye.

Recognizing this deficit with conventional eye wash bottles, several attempts have been made to utilize eyelid retractors to help open the eyelids (see, e.g. U.S. Pat. Nos. 3,872,866 and 5,762,606). However, use of eyelid retractors have not been widely adopted by the industry, partly due to the difficulty of their use.

Hence, there remains a need in the art for an eye washing device that rapidly allows the eye to be flooded with fluid, while allowing an individual to ensure that their eyelid can be opened with a free hand to allow for adequate internal (e.g., in lacrimal sacs and/or under the eye lid) rinsing of the eye. The present invention provides such advantages, and further overcomes many of the shortcomings associated with the prior art.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, the invention relates to a device for washing eyes which permits the user to use one hand to expel fluid from a container, and the other hand to ensure that the eyelids are separated, in order to allow to allow the fluid to adequately rinse under the eye lids. Hence, the eyewash device can be utilized in emergency settings (for example, if the eye is accidentally exposed to an acid or other corrosive material).

Preferred eye wash devices of the present invention comprise a container and a container locater. In use, the container locater is rested against the eyebrow, thereby allowing proper directional control of the fluid with a single hand. It is important to note that the container locater is not designed to hold open the eyelid. Rather, it is designed to allow an individuals' fingers to hold open the eyelid, while still dispensing fluid from the container. The container locater is also designed to allow fluid to drain from the container locater, rather than be retained in a cup. This helps to prevent the eye from being re-washed with dirty or contaminated fluid.

This Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter. Furthermore, the publications discussed above and throughout the text are provided solely for their disclosure prior to the filing date of the present application. Nothing herein is to be construed as an admission that the inventors are not entitled to antedate any referenced publication by virtue of prior invention.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIGS. 2A-2D illustrate several different views of various embodiments, including.

DETAILED DESCRIPTION OF THE INVENTION

Briefly stated, the present invention provides an eye wash device which can be utilized in emergency settings (for example, if the eye is accidentally exposed to an acid or other corrosive material). The eye wash device (comprising a container and a container locater allows an individual to dispense fluid from a container into the eye with the one hand, while holding the eye open with the other hand. The container locater on the container is rest against the eyebrow, thereby allowing proper directional control of the fluid with a single hand.

The present invention can be understood more readily by reference to the following detailed description and reference drawings which disclose preferred embodiments of the invention.

Figure 1:
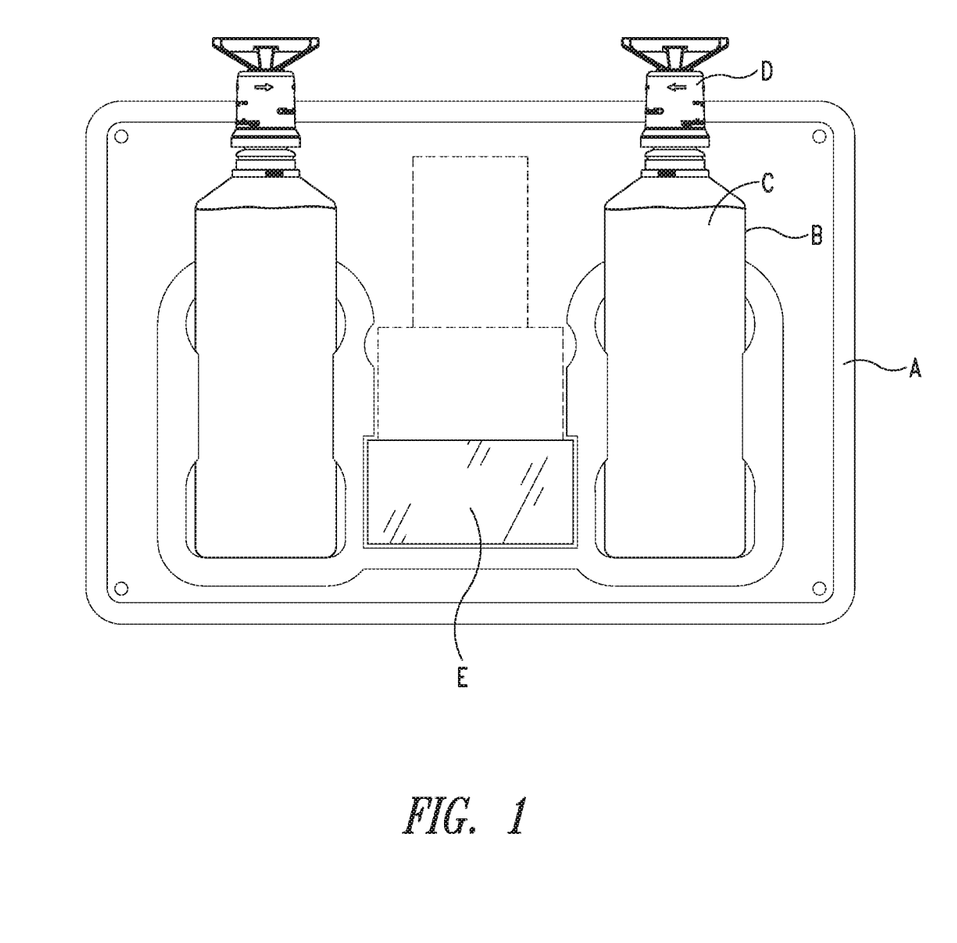
FIG. 1 illustrates a side view of one embodiment of an eye wash device, comprising a holding station and two containers having a container locater on top.

FIG. 1 illustrates a side view of one embodiment of an eye wash device, comprising a holding station A having a container B filled with a suitable fluid C for washing out an eye. A container locater D is attached to the bottle which can be turned in order to open the bottle and allow fluid to be expelled. The holding station A can also have a mirror E in order for a person to more closely examine their own eye.

Figure 2A:
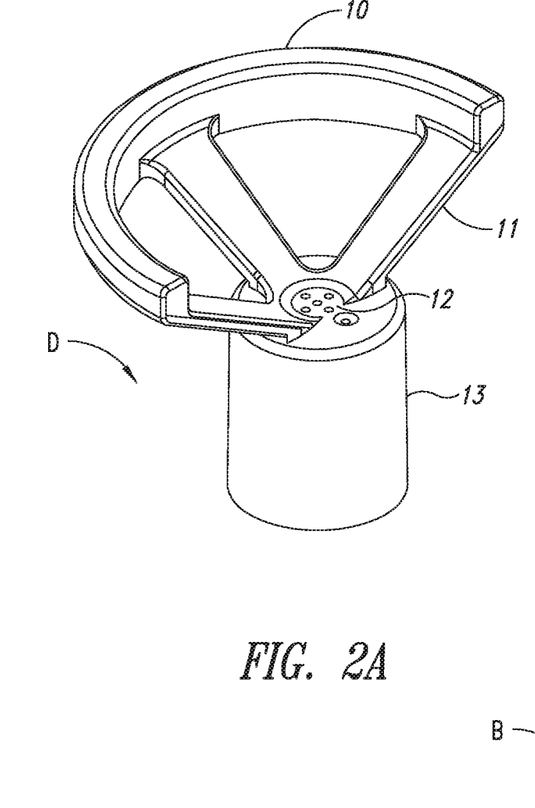
FIGS. 2A and 2D a container locater.

FIG. 2A illustrates one embodiment of a container locater D. This representative container locater has a one-half circular base or guide 10 (an example of an "arced base") for resting on an individual's brow, several struts 11 for supporting the one-half circle base 10 on the cap 13. Several small holes 12 through the cap or fitting 13 allow fluid to be expelled in a controlled manner from a container (not shown). FIG. 2D illustrates a bottom view of container locater D. The bottom of the container locater has a slot suitable for fitting onto a container such as that shown in FIGS. 2B and 2C.

Figure 2B:
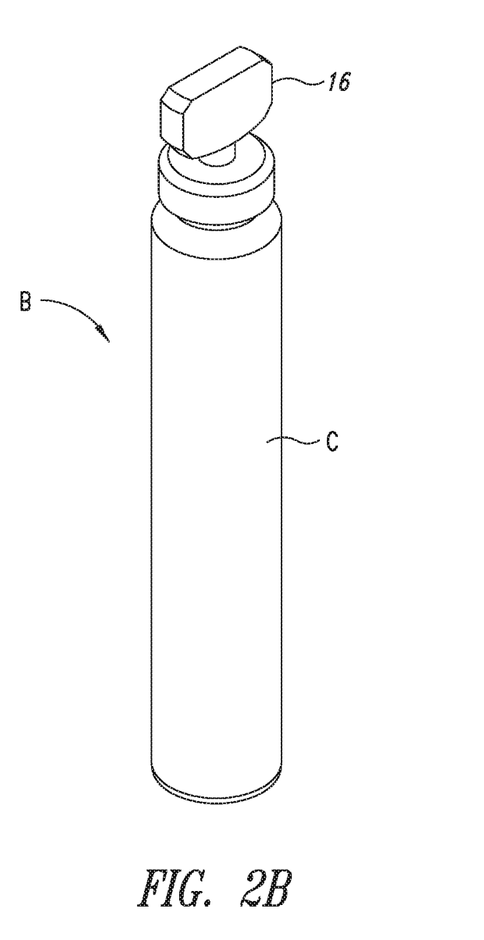
FIGS. 2B and 2C a container having eye wash fluid therein.
Figure 2C:
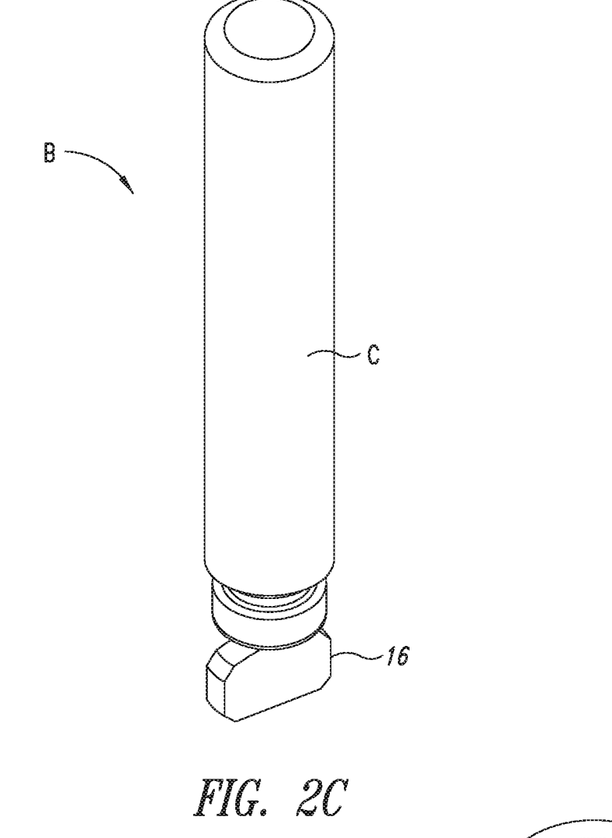
Figure 2D:
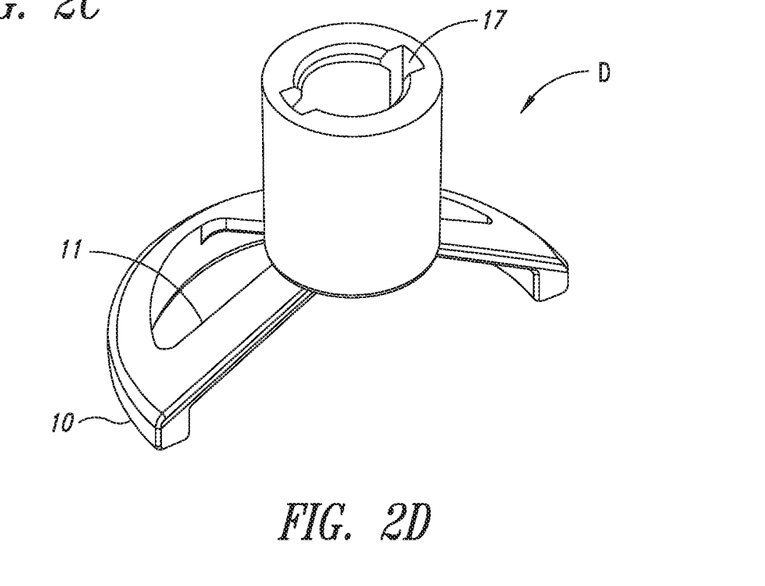

FIGS. 2B and 2C illustrate a container B having fluid C, and an engaging member 16 for engaging the slot 17 in FIG. 2D. This allows the container B to be opened and fluid to be expelled through the container locater D, using a single hand.

Figure 3A:
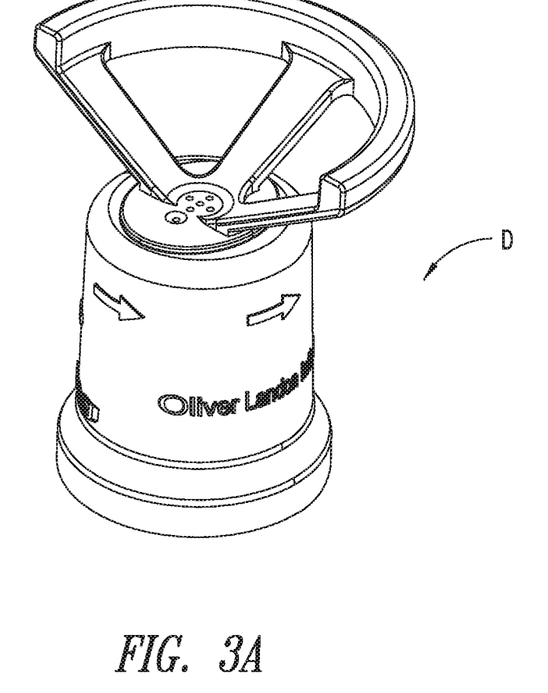
FIGS. 3A-3B illustrate several different views of a representative one-half circle container locater, including FIG. 3A, a side view; and bottom view in FIG. 3B.
Figure 3B:
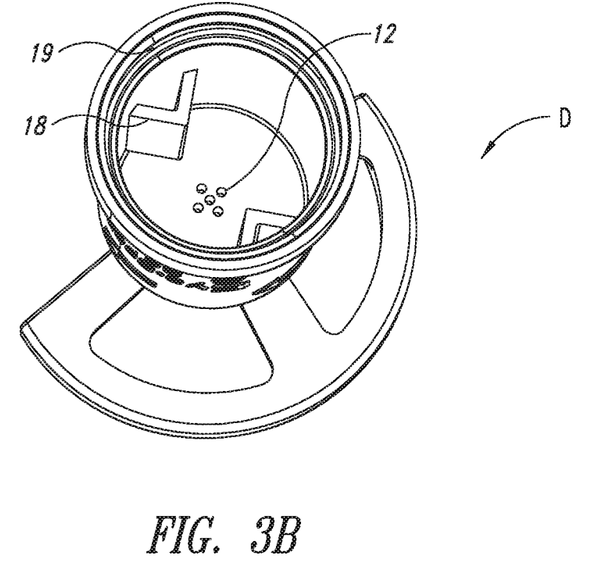

Further representative illustrations of a container locater D are provided in FIGS. 3A and 3B. As shown in FIG. 3B, the container locater D has an engaging element 18 for connecting to a container, thereby allowing the container to be opened by turning of the container locater. In addition, the container locater D has one or more rings 19 (or in alternative embodiments, screw threads) which allow the container locater D to be attached to a container. Small holes 12 can be seen in the bottom of the container locater.

Figure 4:
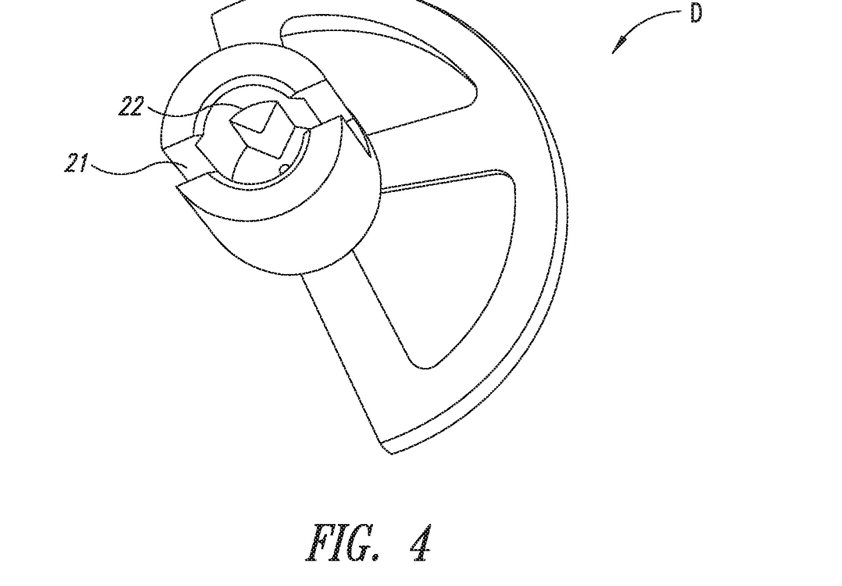
FIG. 4 illustrates a bottom side view of one embodiment of the one-half circle container locater.

FIG. 4 illustrates yet another embodiment of a container locater D, having a slot 21 and an engaging member 22 for connecting to a container.

Figure 5:
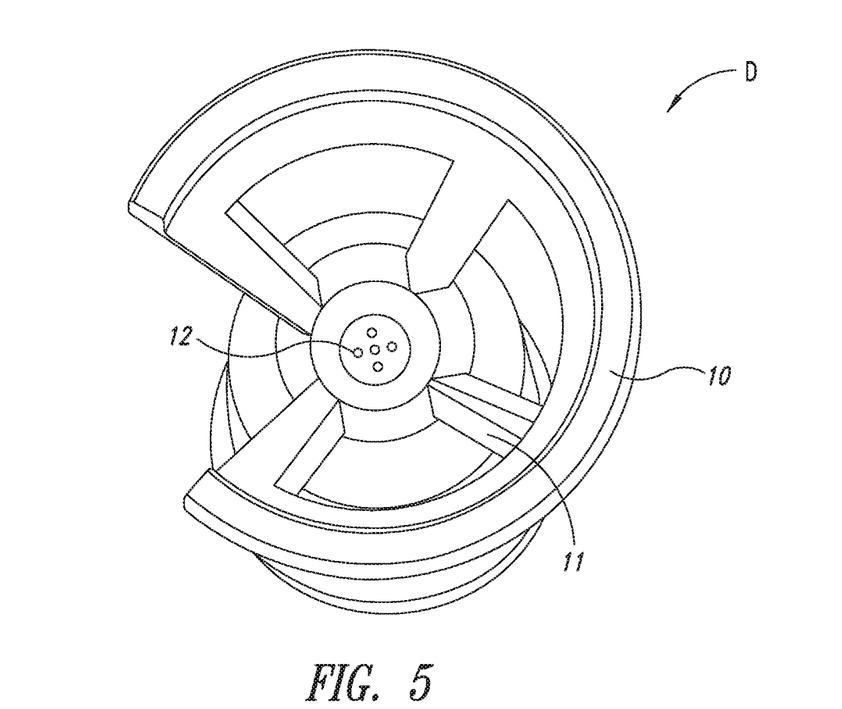
FIG. 5 illustrates a top view of one embodiment of the three-quarters circle container locater.

FIG. 5 illustrates a three-quarter circle container locater D, having a three-quarter circular guide 10 and four supporting members 11. The container locater D also has a plurality of small holes 12 which allow fluid from a container to be expelled through the container locater D.

Figure 6:
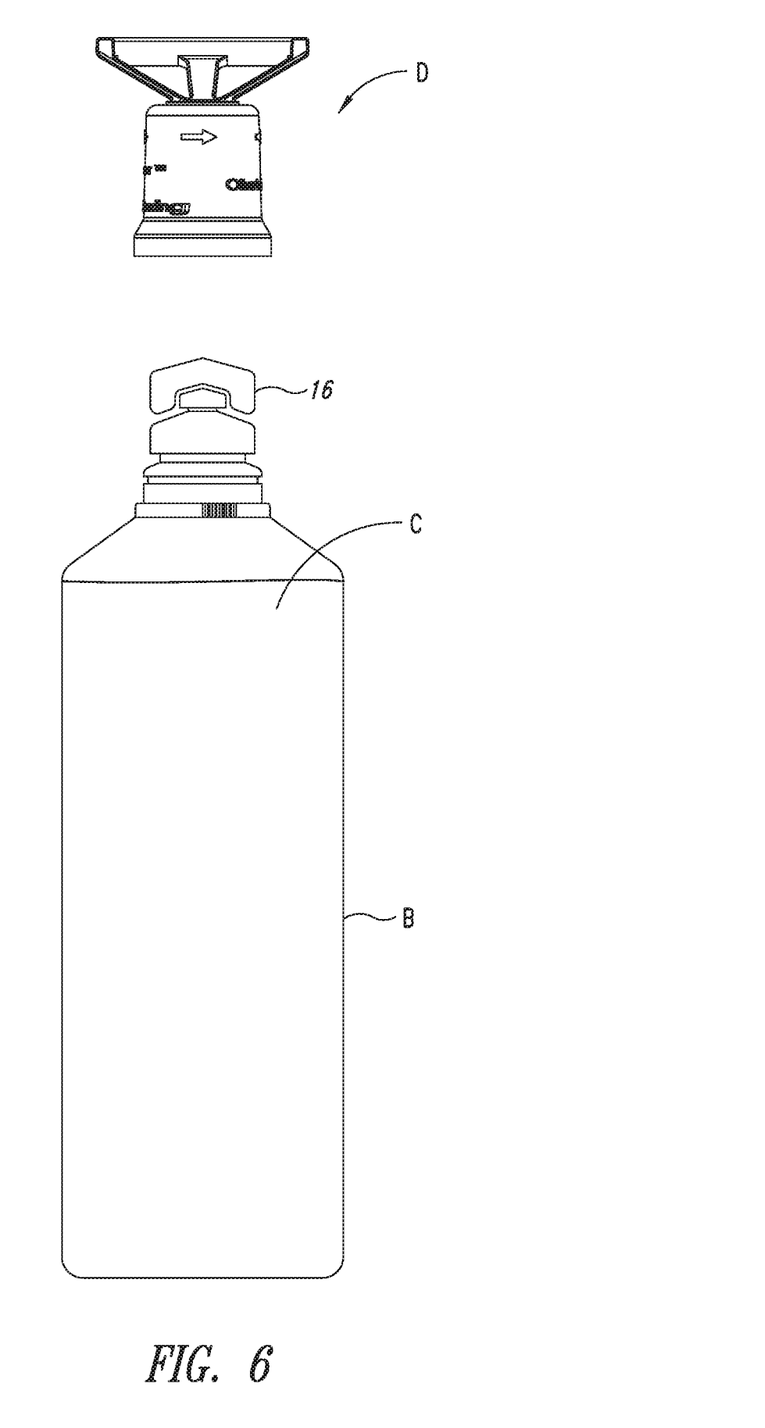
FIG. 6 illustrates a side view of a container bottle with a container locater.

FIG. 6 illustrates a container B having fluid C and a representative slotted member 16 for engaging the container locater D.

As should be readily evident given the disclosure provided herein, variations of the above embodiments may readily be made.

For example, the container locater is typically semicircular in nature, although it can be shaped into different forms, including for example, arcs with less curvature. Within preferred embodiments of the invention the container locater leaves an open space of from one-quarter to one-half of the circle or arc, thereby providing a space for an individual's fingers to hold open the eye while fluid is expelled from the container. Put another way, the container locater can range in size from approximately one-half of a semi-circle or arc, to as much as three-quarters of a semi-circle or arc.

Within preferred embodiments of the invention the container locater has an inner diameter of approximately 50 mm (+/−5 mm) and an outer diameter of approximately 60 mm (+/−5 mm). Within other embodiments of the invention the semi-circular (or arced) base or guide rises approximately 15-20 mm (+/−5 mm, or more preferably 18 or 19 mm (+/−2 mm) from the small hole or holes (through which fluid is expelled). Within further embodiments of the invention the container locater has 1, 2, 3, 4, 5, 6, 7, 8, 9 or 10 or more holes from which fluid can be dispensed or expelled. Within other embodiments, the cap or fitting has between 3 and 6 small holes (or more preferably, 4 or 5 holes) of an average size of 1 mm located through the center of the container locater, and through which fluid can be dispensed or expelled.

Within yet other embodiments of the invention the semi-circular base or guide is supported by one or more struts, or members (e.g., an elongated supporting member which optionally, may be either straight or curved). Within preferred embodiments of the invention, the guide or arced base of the one-half circular (or arc) container locater is supported by two or three struts or elongated supporting members, and the guide or base of the three-quarter (or arc) container locater is supported by three or four struts or elongated supporting members.

Within yet other embodiments of the invention the guide or base of the container locater is supported by one or more members which has numerous holes or spaces between them, or through them. The purpose of creating numerous holes or spaces in this embodiment is to allow fluid that has been dispersed from the container to drain through the container locater, as opposed to be held within it (e.g., as a cup would hold water). Within preferred embodiments of this invention the member which supports the base or guide has holes or spaces which comprise greater than 25%, 30%, 40%, 50%, 60%, 70%, 75%, or 80% of the complete surface area of the supporting member (i.e., if the surface area of the supporting member between the fitting or cap and arced base was completely filled, greater than 25%, 30%, 40%, 50%, 60%, 70%, 75%, or 80% of that total area would comprise empty space or holes)

The container locater can be made utilizing a variety of techniques, including for example, 3D printing and molding. The container locater can also be made of a wide variety of materials, although non-toxic polymeric materials (e.g., polyethylene or polycarbonate) are particularly preferred.

Within certain preferred embodiments of the invention, the container locater is designed to specifically attach to a desired container, and to positively open the container to release the liquid provided therein. In one example, the container locater accepts a slot or other specific mechanism which is attached to the container. When the slot or other mechanism on the container locater is turned or pushed, the attached container is opened (see e.g., FIGS. 2C and 2D, FIGS. 3B and 4, and FIG. 6.

Within other embodiments of the invention the container B as shown in FIG. 6 can be filled (or is prefilled) with a fluid C that is suitable for rinsing any eye. A wide variety of fluids can be utilized in this regard, including for example buffered fluids (e.g., buffered isotonic solutions), saline, and water. The fluids C can be provided in either sterile or non-sterile form (although, within preferred embodiments the water should be clean and suitable for use in rinsing the eye). Within related embodiments of the invention fluid is provided in a container that is at least 15 ml or greater, 500 ml or greater, 500 ml or greater, or 1 liter. Within preferred embodiments of the invention the container holds 1 liter or less, in order to make it easy to lift for most individuals.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A device for washing eyes, comprising a container and a container locater.

2) The device according to embodiment 1, wherein said container locater comprises an arced base, a member for supporting the base, and a fitting having a one or more holes through with fluid can be expelled from said container.

3) The device according to embodiments 1 or 2 wherein said arced base is semicircular (e.g., a quarter circle or quarter of an oval, a half-circle, half of an oval, a three-quarters circle, or three-quarters of an oval). Within further embodiments the arced base can be any arc (continuous or discontinuous) with a total angle of arc ranging from 90 degrees to 360 degrees, or any angle in-between (e.g., from 90 to 180 degrees, 180 degrees, from 180 to 270 degrees, 270 degrees, or from 270 to 360 degrees. Within further embodiments the arc can be disjointed, e.g., a plurality of linear or semi-linear structures which are adjoined to form an arc in aggregate.

4) The device according to any one of embodiments 1 to 3 wherein said member for supporting the arced base has one or more holes, or other spaces through which fluid can pass (e.g., when fluid is expelled from a container locater/container system, the fluid can wash the eye and drain through the supporting member for the arced base). Within yet further embodiments the holes or a space comprise greater than 25%, 30%, 40%, 50%, 60%, 70%, 75%, or 80% of the surface area of the supporting member (e.g., if the member was a solidary supporting structure).

5) The device according to any one of embodiments 1 to 4 wherein said member comprises one or more struts. Within related embodiments the supporting member comprises multiple struts (e.g., 2, 3, or 4 struts) which support the arced base.

6) The device according to any one of embodiments 1 to 5 wherein said container is a 15 ml ampoule, or a 500 ml, 950 ml, or 1 liter bottle. Within related embodiments the container can be any sized ampoule, bottle, a vial, bag, bladder, or, other self-contained storage reservoir for fluid. Representative examples of self-contained systems wherein one or more of the container locaters disclosed herein can be used (e.g., substituted for other conventional eye washing liquid dispersing mechanisms) include those described in U.S. Pat. Nos. 5,850,641, 6,540,726, 7,254,848, 7,857,795, 8,313,472, 8,566,974 and 8,702,663, as well as U.S. Patent Application Nos. 2007/0204398, 2007/0089231, 2008/0281280 and 2009/0043269, all of which are incorporated by reference in their entirety.

7) The device according to any one of embodiments 1 to 5 wherein said container is a plumbed system which release water upon activation (see e.g., EP3067036, which is hereby incorporated by reference in its entirety). Hence, one or more of the container locaters described herein can be utilized on a plumbed eye-washing system as well.

8) The device according to any one of embodiments 1 to 6 wherein said container is filled with fluid. Within certain embodiments of the invention the fluid is sterile.

9) A container locater as described in any one of embodiments 1 to 8. Within further embodiments the device and/or container locater as described in any one of the previous embodiments is sterile. Within further embodiments the container locater may be removably coupled to a container or self-contained system as described herein. Within alternative embodiments, the container locater may be permanently coupled to a container. Within yet other embodiments, the container locater may be affixed (removably or permanently) to a plumbed system which releases water upon activation.

10) A method of washing an eye, comprising the step of expelling fluid from a device according to any one of embodiments 1 to 9 into an individual's eye, thereby washing the eye.

11) The method of embodiment 10, further comprising the step of holding open said individual's eyelid.

12) The method according to embodiments 10 or 11, wherein an individual uses one hand to hold open their eyelid, and their other hand to expel fluid from the device according to any one of embodiments 1 to 9.

13) The method according to anyone of embodiments 10 to 12, wherein, prior to washing, said individual's eye has been subjected to a chemical or particulate hazard.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A device for washing eyes, comprising:
    a container containing a fluid suitable for rinsing eyes,
        wherein the container includes a first engaging member extending from a top of the container,
        wherein the container is closed to prevent discharge of the fluid from the container until the device is operational; and
    a container locator comprising:
        a cap configured to be coupled with the container, said cap including one or more holes through which the fluid is expelled from said container,
        an arced base sized to rest against a user's eyebrow region to thereby allow directional control of the fluid with a first hand of a user and to further allow the user to open an eyelid of an eye with a second hand,
            wherein in instructed usage, the container locator is not designed to hold open the eyelid,
        a base-supporting member extending from the cap to the arced base for supporting the arced base on the cap, and
        a second engaging member recessed within the cap and having a shape configured to securely receive the first engaging member,
            wherein the container locator attaches to the container by interfacing the first engaging member within the second engaging member and rotating the container locator relative to the container such that the second engaging member of the container locator causes the first engaging member of the container to rotate in the same direction as the container locator relative to the container, causing the container to open and allowing the fluid to be expelled from the container when the container locator attaches to the container.

2. The device according to claim 1, wherein the container locator further comprises at least one ring within the cap to attach the container locator to the container.

3. The device according to claim 2 wherein said arced base is a semicircular shape.

4. The device according to claim 3 wherein said semicircular shape is a half-circle.

5. The device according to claim 3 wherein said semicircular shape is a three-quarters circle.

6. The device according to claim 1, wherein said base-supporting member has one or more spaces.

7. The device according to claim 1, wherein said base-supporting member comprises one or more struts.

8. The device according to claim 1 wherein said container is a one liter bottle.

9. The device according to claim 1 wherein said container is a 15 ml ampoule.

10. The device according to claim 1, further comprising a holding station for holding the container and the container locator while not in use.

11. The device according to claim 1, wherein the one or more holes comprises a plurality of holes.

12. The device according to claim 1, wherein the one or more holes comprises 3-6 holes.

13. The device according to claim 1, wherein each of the one or more holes has an average size of 1 mm.

14. The device according to claim 1, wherein the second engaging member is integral with the cap.

15. The device according to claim 1, wherein the arced base does not hold open the user's eyelid.

16. A method of using an eye-washing device, the eye-washing device comprising a container containing a fluid suitable for rinsing eyes and a container locator comprising a cap with a base-supporting member supporting extending from the cap to an arced base sized to rest against a user's eyebrow region and one or more holes in the cap through which the fluid is expelled from said container, the method comprising:
  attaching the container locator to the container by interfacing a second engaging member of the container locator with a first engaging member of the container and rotating the container locator relative to the container such that the second engaging member causes the first engaging member to rotate in the same direction as the container locator, thereby causing the container to open when the container locator is rotatably attached to the container, allowing the fluid to be expelled from the container;
  holding, with a first hand, the container coupled with the container locator;
  resting the arced base against the user's eyebrow region while holding the container with the first hand, wherein the container locator is not designed to hold open a user's eyelid, thereby aligning the one or more holes with an eye to be washed;
  holding open the eye to be washed with a second hand;
  expelling the fluid from the container through the one or more holes in the container locator into the eye.

17. The method of claim 16, wherein the container locator is secured to the container by engaging one or more rings of the container locator with the container.

18. The method according to claim 17, wherein holding open the eye to be washed with the second hand includes extending at least one finger of the second hand through one or more spaces in the base-supporting member to access the eye.

* * * * *